United States Patent [19]

Adams et al.

[11] Patent Number: 5,258,493

[45] Date of Patent: Nov. 2, 1993

[54] CYCLIC PEPTIDES FOR TREATING HERPES INFECTIONS

[75] Inventors: Julian Adams, Ridgefield, Conn.; John DiMaio, Montreal; Raymond Plante, Laval, both of Canada

[73] Assignee: Bio-Mega/Boehringer Ingelheim Research Inc., Laval, Canada

[21] Appl. No.: 853,360

[22] Filed: Mar. 16, 1992

Related U.S. Application Data

[62] Division of Ser. No. 547,721, Jul. 3, 1990, Pat. No. 5,149,778.

[30] Foreign Application Priority Data

Jul. 7, 1989 [CA] Canada ................................. 605070

[51] Int. Cl.$^5$ ................................................ C07K 7/54
[52] U.S. Cl. ................................ 530/317; 930/270; 930/DIG. 536
[58] Field of Search ....................... 530/317, 321

[56] References Cited

U.S. PATENT DOCUMENTS 4,814,432 3/1989 Freidinger et al. ............... 530/329

*Primary Examiner*—Y. Christina Chan
*Attorney, Agent, or Firm*—D. E. Frankhouser; D. Reitenbach; M-E. M. Timbers

[57] ABSTRACT

Disclosed herein are cyclic peptide derivatives of the formula

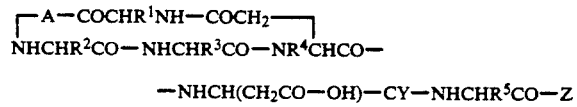

$$-NHCH(CH_2CO-OH)-CY-NHCHR^5CO-Z$$

wherein A is absent or the tripeptide radical Thr←Gly←Ala, $R^1$ is benzyl or benzyl monosubstituted at position 4 of the aromatic ring with halo, hydroxy, lower alkyl or lower alkoxy, $R^2$ and $R^4$ each independently is hydrogen or lower alkyl, $R^3$ is lower alkyl or lower alkyl monosubstituted with a hydroxy, $R^5$ is lower alkyl, Y is oxo or thioxo and Z is hydroxy or $NR^6R^7$ wherein $R^6$ and $R^7$ each independently is hydrogen or lower alkyl. The derivatives are useful for treating herpes infections.

1 Claim, No Drawings

CYCLIC PEPTIDES FOR TREATING HERPES INFECTIONS

This is a division of application Ser. No. 547,721, filed Jul. 3, 1990, now U.S. Pat. No. 5,149,778.

FIELD OF THE INVENTION

This invention relates to cyclic peptide derivatives having antiviral properties and to means for using the derivatives to treat viral infections. More specifically, the invention relates to cyclic peptide derivatives (hereinafter called "peptides" or "cyclic peptides") exhibiting activity against herpes viruses, to pharmaceutical compositions comprising the peptides, and to a method of using the peptides to treat herpes infections.

BACKGROUND OF THE INVENTION

The family of herpes viruses is responsible for a wide range of infections that afflict humans and many important domestic animals. The diseases caused by these viruses range from bothersome cold sores to highly destructive infections of the central nervous system (encephalitis). The more common members of this family include herpes simplex virus (types 1 and 2) responsible for cold sores and genital lesions; varicella zoster virus which causes chicken pox and shingles; and Epstein-Barr virus which causes infectious mononucleosis. Although some significant advances have been made in the last decade in antiviral therapy, the need for effective, safe therapeutic agent for treating herpes viral infections continues to exist. For a recent review of current therapeutic agents in this area, see M. C. Nahata, "Antiviral Drugs: Pharmacokinetics, Adverse Effects and Therapeutic Use", J. Pharm. Technol., 3, 100 (1987).

The present application discloses a group of cyclic peptide derivatives having activity against herpes viruses. The relatively selective action of these peptides against herpes viruses, combined with a wide margin of safety, renders the peptides as desirable agents for combating herpes infections.

The association of peptides with anti-herpes activity is uncommon. Instances of reports of such an association include B. M. Dutia et al., Nature, 321, 439 (1986), E. A. Cohen et al., Nature, 321, 441 (1986), J. H. Subak-Sharpe et al., UK patent application 2185024, published Jul. 8, 1987, E. A. Cohen et al., European patent application 246630, published Nov. 25, 1987, R. Freidinger et al., European patent application 292255, published Nov. 23, 1988, and R. Freidinger et al., U.S. Pat. No. 4,814,432, issued Mar. 21, 1989. The subject peptides of the previous reports can be distinguished from the peptides of the present application by characteristic structural and biological differences.

SUMMARY OF THE INVENTION

The cyclic peptides of this invention are represented by formula 1

wherein A is absent or the tripeptide radical Thr←Gly←Ala; $R^1$ is benzyl or benzyl monosubstituted at position 4 of the aromatic ring with halo, hydroxy, lower alkyl or lower alkoxy; $R^2$ and $R^4$ each independently is hydrogen or lower alkyl; $R^3$ is lower alkyl or lower alkyl monosubstituted with a hydroxy; $R^5$ is lower alkyl; Y is oxo or thioxo; and Z is hydroxy or $NR^6R^7$ wherein $R^6$ and $R^7$ each independently is hydrogen or lower alkyl; or a therapeutically acceptable salt thereof.

A preferred group of the peptides of this invention is represented by formula 1 wherein A and $R^1$ are as defined hereinabove, $R^2$ is 1-methylethyl, 1-methylpropyl or 2-methylpropyl, $R^3$ is 1-methylethyl, 1-methylpropyl, 2-methylpropyl or 1-hydroxyethyl, $R^4$ is hydrogen or methyl, $R^5$ is 2-methylpropyl, and Y and Z are as defined hereinabove; or a therapeutically acceptable salt thereof.

A more preferred group of peptides is represented by formula 1 wherein A, $R^2$, $R^3$, $R^4$, $R^5$, Y and Z are as defined in the last instance and $R^1$ is (4-halophenyl)methyl, (4-hydroxyphenyl)methyl, (4-methylphenyl)methyl or (4-methoxyphenyl)methyl, or a pharmaceutically acceptable salt thereof.

A most preferred group of peptides is represented by formula 1a

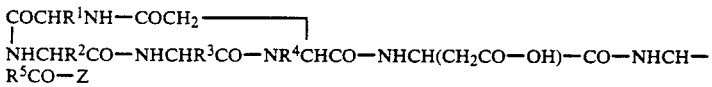

wherein $R^1$, $R^2$, $R^3$, $R^4$ and $R^5$ are as defined in the last instance, or a therapeutically acceptable salt thereof.

Another preferred group of peptides is represented by formula 1b

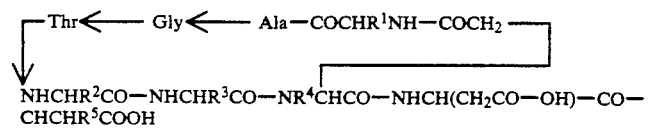

wherein $R^1$, $R^2$, $R^3$, $R^4$ and $R^5$ are as defined in the last instance, or a therapeutically acceptable salt thereof.

Included within the scope of this invention is a pharmaceutical composition comprising an anti-herpes virally effective amount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective amount of the peptide of formula 1, or a therapeutically acceptable salt thereof.

Another important aspect involves a method of inhibiting the replication of herpes virus by contacting the virus with a herpes viral ribonucleotide reductase inhibiting amount of the peptide of formula 1, or a therapeutically acceptable salt thereof.

Processes for preparing the cyclic peptides of formula 1 are described hereinafter.

DETAILS OF THE INVENTION

GENERAL

It is to be understood that when the symbol A of formula 1 hereinabove and formulae 2, 3 and 4 hereinafter is absent then a direct bond joins the nitrogen atom (N) and the carbon atom(C) to which A is shown schematically to be attached. Also, when A represents the tripeptide divalent radical Thr←Gly←Ala, the N-terminus of the tripeptide radical is attached to the above noted carbon atom and the C-terminus is attached to the above-noted nitrogen atom.

The term 'residue' with reference to an amino acid or amino acid derivative means a radical derived from the corresponding α-amino acid by eliminating the hydroxyl of the carboxy group and one hydrogen of the α-amino group.

In general, the graphic representations and the abbreviations used herein for designating the amino acids and the protective groups are based on recommendations of the IUPAC-IUB Commission of Biochemical Nomenclature, see European Journal of Biochemistry 138, 9 (1984). For instance, Gly, Val, Thr, Ala, Ile, Asp and Leu represent the residues of glycine, L-valine, L-threonine, L-alanine, L-isoleucine, L-aspartic acid, and L-leucine, respectively.

The asymmetric carbon atoms residing in the cyclic framework and the principal linear axis of the side arm (i.e. the backbone) of the cyclic peptides of formula 1, exclusive of the Z terminal groups, have an S configuration. Asymmetric carbon atoms residing in the side chain of an amino acid residue may also have the R configuration.

The term 'halo' as used herein means a halo radical selected from bromo, chloro, fluoro or iodo.

The term "lower alkyl" as used herein, either alone or in combination with a radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tertiary-butyloxy.

Additional abbreviations or symbols used hereafter are:

| | |
|---|---|
| Boc | 1,1-dimethylethoxycarbonyl or tertiary-butyloxycarbonyl |
| BOP | (benzotriazol-1-yloxy)tris(dimethylamino)-phosphonium hexafluorophosphate |
| Bzl | benzyl |
| 2,6-diClBzl | 2,6-dichlorobenzyl |
| Bu$^t$ | tertiary butyl |
| Fmoc | 9-fluorenylmethoxycarbonyl |
| HOBt | 1-hydroxybenzotriazole |
| OCH$_3$ | methoxy |

The symbol "ψ[CSNH]" used between the three letter representations of two amino acid residues means that the normal amide bond between those residues in the peptide, being represented, has been replaced with a thioamide bond.

The term "pharmaceutically acceptable carrier" or "veterinarily acceptable carrier" as use herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "coupling agent" as used herein means an agent capable of effecting the dehydrative coupling of an amino acid or peptide free carboxy group with a free amino group of another amino acid or peptide to form an amide bond between the reactants. Similarly, such agents can effect the coupling of an acid and an alcohol or amine to form a corresponding ester or amide, respectively. The agents promote or facilitate the dehydrative coupling by activating the carboxy group. Descriptions of such coupling agents and activated groups are included in general text books of peptide chemistry; for instance, E. Schroder and K. L. Lubke, "The Peptides", Vol. 1, Academic Press, New York, N.Y., 1965, pp 2-128, and K. D. Kopple, "Peptides and Amino acids", W. A. Benjamin, Inc., New York, N.Y., 1966, pp 33-51. Examples of coupling agents are thionyl chloride, diphenylphosphoryl azide, 1,1'-carbonyldiimidazole, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris(dimethylamino)-phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole.

PROCESS

The peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schroder and K. Lubke, cited above, in the textbook series, "The Peptides: Analysis, Synthesis, Biology", E. Gross et al, Eds., Academic Press, New York, N.Y., 1979-1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptides is the protection of the reactive side chain groups of the various amino acid residues or derived amino acid residues with suitable protective groups which will prevent a chemical reaction from occurring at that site until the protective group is ultimately removed. Usually also common is the protection of an α-amino group on an amino acid or a fragment while that entity reacts at the carboxy group, followed by the selective removal of the α-amino protective group to allow subsequent reaction to take place at that location. Usually another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

A key factor for the process is a branched, protected intermediate having the amino acid sequence of the final product and having two selectively removable protective groups which can be removed in the presence of other protective groups on the intermediate. One of these protective groups protects the terminal α-amino and the other protects the side chain carboxy of the amino acid residue (Asp) which eventually forms the bridgehead of the final product. By selectively removing these two protective groups from this key intermediate, noted hereinafter as the protected linear peptide of formula 2, the resultant branched intermediate can be intramolecularly cyclized, via coupling of the freed terminal α-amino and the freed side chain carboxyl, to afford the cyclic framework of the final product.

More specifically, the peptides of formula 1 can be prepared by:

(a) forming a protected linear peptide of formula 2

$$X^1-NHCHR^{14}CO-A^1-NHCHR^2CO-NHCHR^3CO-NR^4CH(CH_2CO-OX^2)- \atop CO-NHCH(CH_2CO-OX^3)-CY-NHCHR^5CO-Z^1 \qquad 2$$

wherein $R^2$, $R^3$, $R^4$, $R^5$ and Y are as defined herein, $A^1$ is absent or Thr($R^8$)←Gly←Ala wherein $R^8$ is a protective group for the hydroxyl of Thr, $R^{14}$ is benzyl or benzyl monosubstituted at position 4 of the aromatic ring with halo, lower alkyl, lower alkoxy or $OR^9$ wherein $R^9$ is a protective group for a phenolic hydroxyl, $X^1$, $X^2$ and $X^3$ are protective groups and $Z^1$ is OH protected by a carboxy protecting group or is $NR^6R^7$ wherein $R^6$ and $R^7$ are as defined herein, by the stepwise coupling of appropriate amino acid residues or peptide fragments in the order of the amino acid sequence of the linear peptide, and if required, by amidating the corresponding C-terminal carboxyl of the protected peptide so obtained, (b) selectively removing the $X^1$ and $X^2$ protective groups of the protected peptide of formula 2 in the presence of other protective groups on the protected peptide to obtain the protected peptide of formula 3

$$NH_2CHR^{14}CO-A^1-NHCHR^2CO-NHCHR^3CO-NR^4CH(CH_2CO-OH)- \atop CO-NHCH(CH_2CO-OX^3)-CY-NHCHR^5CO-Z^1 \qquad 3$$

wherein $A^1$, $R^{14}$, $R^2$, $R^3$, $R^4$, $R^5$, $X^3$, Y and $Z^1$ are as defined herein, (c) cyclizing the protected peptide of formula 3 with a coupling agent to obtain the protected cyclic peptide of formula 4

$$\begin{array}{c}\ulcorner A^1-COCHR^{14}NH-COCH_2\urcorner\\ NHCHR^2CO-NHCHR^3CO-NR^4CHCO-NHCH(CH_2CO-OX^3)-CY-NHC-\\ HR^5CO-Z^1\end{array} \qquad 4$$

wherein $A^1$, $R^{14}$, $R^2$, $R^3$, $R^4$, $R^5$, $X^3$, Y and $Z^1$ are as defined herein, and (d) removing the remaining protective groups, $X^3$ and $Z^1$ and $R^6$ and $R^7$ if present, of the protected cyclic peptide to obtain the corresponding peptide of formula 1; and, if desired, transforming the peptide of formula 1 into a therapeutically acceptable salt.

Convenient and effective protective groups for the preceding process are Bzl or 2,6-diClBzl for $R^8$ and $R^9$, Boc for $X^1$, $Bu^t$ for $X^2$, Bzl or 2,6-diClBzl for $X^3$ and lower alkoxy or benzyloxy for $Z^1$.

The protected linear peptide of formula 2 wherein Y is oxo and $Z^1$ is lower alkoxy or benzyloxy can be prepared as follows: A first amino acid residue, e.g. Boc-Leu-OH, is coupled to a photolabile resin to give the corresponding α-amino protected amino acid-resin. The α-amino protective group of the latter is removed to give the corresponding amino acid-resin with a free amino group. Thereafter, a first protected aspartic acid residue, e.g. Boc-Asp(OBzl)—OH, and a second protected (bridgehead) aspartic acid residue, e.g. Fmoc-Asp(OBu$^t$)—OH, are coupled serially to the amino acid resin to give the corresponding protected tripeptide-resin, e.g. Fmoc-Asp(OBu$^t$)—Asp(OBzl)—Leu—O-resin. Selective removal of the α-amino protecting group of tripeptide-resin, and subsequent serial coupling up to and including the pentultimate coupling of the appropriate α-amino protected amino acid residues in which the α-amino protecting group is one which can be selectively removed in the presence of the other protecting groups on the growing peptide-resin during each coupling step, e.g. the baselabile Fmoc protective group; followed by a final coupling of the N-terminal α-amino protected amino-acid residue, e.g. Boc-Tyr(2,6-diClBzl)-OH, in which the α-amino protecting groups ($X^1$) is one which can be selectively removed along with the side chain protecting group ($X^2$) on the bridgehead aspartic acid residue, yields the corresponding protected linear peptide-resin having the complete sequence of the desired peptide, e.g. Boc-Tyr(2,6-diClBzl)-Val-Ile-Asp(OBu$^t$)-Asp(OBzl)-Leu-O-resin.

The term "photolabile resin" or the term "resin" (used as a radical in combination with a protected peptide) refers to resins which when incorporated into a peptide-resin system allow the peptide to be cleaved selectively from the system by photolysis. Examples of such resins are 4-(2-bromo- or 4-(2-chloro-propionyl)-phenoxyacetyl BHA resins described by Bellof and M. Mutter, Chemia, 39, 317 (1985) and by J. Gauthier, Canadian patent application, SN 547,394, filed Sep. 21, 1987.

In the next step, the linear protected peptide is cleaved from the aforementioned protected linear peptide-resin by photolysis. When the protected linear peptide is formed from a 4-(2-bromo- or 4-(2-chloro-propionyl)-phenoxyacetyl BHA resin, noted above, the photolysis is accomplished by dissolving or suspending the protected peptide-resin in a photolytically stable liquid medium; for example, dioxane, dimethylformamide, methanol, ethanol or N-methylpyrrolidine; purging the solution or suspension of the peptide-resin with argon or nitrogen to remove any dissolved oxygen; and then irradiating the suspension or solution with photolytically effective ultraviolet light. In practice, irradiation at a wavelength of 350 nm has been found to be effective. In this manner, the corresponding free C-terminal carboxy derivative of the protected linear peptide of formula 2 is obtained, e.g. Boc-Tyr-(2,6-diClBzl)-Val-Ile-Asp(OBu$^t$)-Asp(OBzl)-Leu-OH. The latter compound is esterified by conventional methods to give the protected linear peptide of formula 2 in which Y is oxo and $Z^1$ is lower alkoxy or benzyloxy.

The corresponding protected linear peptide of formula 2 wherein Y is thioxo and $Z^1$ is lower alkoxy or benzyloxy can be prepared conveniently by solution phase peptide synthesis beginning with a protected dipeptide of formula NH$_2$CH(CH$_2$COX$^3$-)—CY—NHCHR$^4$COZ$^1$ wherein R$^4$, OX$^3$ and $Z^1$ are as defined herein and Y is thioxo. An example such as protected dipeptide is Boc-Asp(OBzl)ψ[CSNH]Leu-OBzl. The latter dipeptide is prepared readily by treating Boc-Asp(OBzl)-Leu-OBzl with LAWESSON'S reagent (2,4-bis(4-methoxyphenyl)-1,3,2,4-dithiadiphosphetane 2,4-disulfide), see U. Pederson et al. Tetrahedron, 38, 3267 (1962). Subsequent coupling in solution of the same amino acid residues as described hereinbefore beginning with the second aspartic acid residue (e.g. Fmoc-Asp(OBu$^t$)-OH and ending with the N-terminal protected amino acid residue, e.g. Boc-Tyr(2,6-diClBzl)-OH, gives the desired protected linear peptide of formula 2 in which Y is thioxo (e.g. Boc-Tyr(2,6-DiCl-Bzl)-Val-Ile-Asp-(OBu$^t$)-Asp(OBzl)ψ[CSNH-]Leu-OBzl.

For the preparation of the peptides of formula 1 wherein Z is NR$^6$R$^7$ as defined herein, the protected cyclic peptide of formula 4 in which A$^1$, R$^{14}$, R$^2$, R$^3$, R$^4$, R$^5$, X$^3$ and Y are as defined herein and $Z^1$ is lower alkoxy or benzyloxy can be hydrolyzed to the corresponding free acid, e.g. Boc-Tyr(2,6-diClBzl)-Val-Ile-Asp(OBu$^t$)-Asp(OBzl)-Leu-OH. Thereafter, the latter compound is coupled with benzylamine or the appropriate lower alkylamine, e.g. methylamine or ethylamine, or the appropriate di(lower alkyl)amine, e.g. dimethylamine or ethylmethylamine, to yield the respective protected amide. Conventional deprotection of the protected amide affords the corresponding C-terminal primary, secondary or tertiary amide of formula 1.

For example, when benzylamine is coupled as such, hydrogenolysis or treatment with hydrofluoric acid affords the corresponding peptide of formula 1 in which Z is NH$_2$.

Turning now to the conversion of the protected linear peptide of formula 2 to the corresponding peptide of formula 1, a convenient mode of achieving the conversion is illustrated as follows: The protected linear peptide of formula 2 in which A$^1$ is absent or Thr(Bzl)←Gly←Ala, R$^{14}$ is benzyl monosubstituted at position 4 of the aromatic ring with O-2,6-diClBzl, R$^2$, R$^3$, R$^4$, R$^5$ and Y are as defined herein, X$^1$ is Boc, X$^2$ is φBut, X$^3$ is φBzl and $Z^1$ is OCH$_3$ is deprotected selectively (i.e. the Boc and φBut protective groups are removed) in 25% to 50% trifluoroacetic acid in methylenedichloride or dimethylformamide at a temperature ranging from 0° to 25° C. to give the corresponding protected linear peptide of formula 3 wherein X$^3$ is φBzl, $Z^1$ is OCH$_3$ and A$^1$, R$^{14}$, R$^2$, R$^3$, R$^4$, R$^5$ and Y are as defined in the last instance.

In the next step, the latter protected linear peptide of formula 3 is cyclized by coupling the terminal amino group and the side chain carboxyl of the bridgehead Asp residue to yield the corresponding protected cyclic peptide of formula 4 wherein A$^1$, R$^{14}$, R$^2$, R$^3$, R$^4$, R$^5$, X$^3$ and Y are as defined in the last instance and $Z^1$ is OCH$_3$. The cyclization is accomplished effectively by adding slowly over a period of two to four hours a solution of the protected linear peptide of formula 3 in an inert solvent containing 6 to 12 molar equivalents of an organic base, preferably diisopropylethylamine, to a solution of a coupling agent, preferably BOP (2 to 4 molar equivalents). The reaction mixture is kept at 10° to 35° C. during the addition. Suitable inert solvents for the aforementioned two solutions include methylenedichloride, dimethylformamide or mixtures thereof. Removal of the solvent from the reaction mixture affords the desired protected cyclic peptide.

The latter compound is subjected to hydrogenolysis (e.g. H$_2$, 5% Pd/C in dimethylformamide and ethanol) to effect the removal of the benzyl protective group of the Asp residue and the 2,6-dichlorobenzyl protective group of the Tyr residue to give corresponding methyl ester of the desired peptide of formula 1 in which Z is hydroxy. Conventional hydrolysis of the methyl ester yields the desired peptide of formula 1 in which Z is hydroxy. Convenient and efficient hydrolysis conditions involve the use of lithium hydroxide or sodium hydroxide in aqueous methanol.

The peptide of formula 1 of this invention can be obtained in the form of a therapeutically acceptable salt.

In the instance where a particular peptide has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, examples of such salts are those with the sodium, potassium or calcium cations, or with strong organic bases, for example, triethylamine or N-methylmorpholine.

ANTIHERPES ACTIVITY

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV), Epstein-Barr virus (EBV), equine herpes virus (EHV) and cytomegalovirus.

Noteworthy is the fact that all of the aforementioned viruses are dependent on their own ribonucleotide reductase to synthesize deoxyribonucleotides for their replication. Although this fact may not be directly linked with the antiviral activity found for the present peptides, the latter compounds have been shown so far to have antiviral properties against all viruses dependent on ribonucleotide reductase to synthesis DNA for their replication.

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula 1 on viral replication is the cell culture technique; see, for example, T. Spector et al., Proc. Natl. Acad. Sci. USA, 82, 4254 (1985).

The therapeutic effect of the peptides can be demonstrated in laboratory animals, for example, by using an assay based on genital herpes infection in Swiss Webster mice, described by E. R. Kern, et al., Antiviral Research, 3, 253 (1983).

When a peptide of this invention, or one of its therapeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the peptide, chosen route of administration and standard biological practice. For topical administration, the peptide can be formulated in pharmaceutically accepted vehicles containing 0.1 to 10 percent, preferably 0.5 to 5 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 16th ed, Mack Publishing Company, Easton, Pa., 1980.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or part of the oral or genital cavity, in an amount sufficient to cover the infected area. The treatment should be repeated, for example, every four to six hours until lesions heal. Healing results usually within 3 to 4 days. No contraindications have been observed.

With reference to systemic administration, the peptide of formula 1 is administered at a dosage of 100 mcg to 1000 mcg per kilogram of body weight per day, although the aforementioned variations will occur. However, a dosage level that is in the range of from about 200 mcg to 500 mcg per kilogram of body weight per day is most desirably employed in order to achieve effective results.

Another aspect of this invention comprises a cosmetic composition comprising a herpes viral prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the peptide than corresponding pharmaceutical compositions for topical application. A preferred range of the amount of the peptide in the cosmetic composition is 0.01 to 0.2 percent by weight.

Although the formulation disclosed hereinabove are effective and relatively safe medications for treating herpes viral infections, the possible concurrent administration of these formulations with other antiviral medications or agents to obtain beneficial results is not excluded. Such other antiviral medications or agents include acyclovir and antiviral surface active agents or antiviral interferons such as those disclosed by S. S. Asculai and F. Rapp in U.S. Pat. No. 4,507,281, Mar. 26, 1985.

The following examples illustrate further this invention. Solution percentages or ratios express volume to volume relationship, unless stated otherwise. Abbreviations used in the examples include Boc: t-butyloxycarbonyl; BOP: (benzotriazol-1-yloxy)tris(dimethylamino)-phosphonium hexafluorophosphate; $Bu^t$: tertiary butyl; Bzl: benzyl; $CH_2Cl_2$: methylenedichloride; DIPEA: diisopropylethylamine; DCC: N,N'-dicyclohexylcarbodiimide; DMF: dimethyl formamide; $Et_2O$: diethyl ether; EtOH: ethanol; Fmoc: 9-fluorenylmethoxycarbonyl; HOBt: 1-hydroxybenzotriazole; HPLC: high performance liquid chromatography; MeOH: methanol; TFA: trifluoroacetic acid. Temperatures are given in degrees centigrade.

EXAMPLE 1

Preparation of the cyclic peptide of the formula

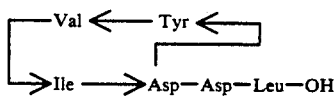

(The peptide of formula 1a wherein $R^1$ is (4-hydroxyphenyl)methyl, $R^2$ is 1-methylethyl, $R^3$ is 1-methylpropyl, $R^4$ is hydrogen and $R^5$ is 2-methylpropyl).

The title compound was synthesized by a modification of the solid-phase method of R. B. Merrifield, J. Amer. Chem. Soc., 85, 2149 (1963). Applying the method, the corresponding protected linear hexapeptide-resin having the correct sequence of amino acid residues was assembled by stepwise addition of the appropriate amino acid residues to [4-{2-(Boc-leucyl)-propionyl}phenoxy]acetamidomethyl-copoly(styrene-1% divinylbenzene) resin. The following protocol was used: (a) Boc-deprotection: 30% TFA in $CH_2Cl_2$ (2 times, firstly for 5 min then for 25 min) or Fmoc-deprotection (20% piperidine in $CH_2Cl_2$ for 10 to 20 min); (b) wash: $CH_2Cl_2$ (3 times for 2 min) (c) wash: isopropanol (2 min); (d) neutralization: 5% DIPEA in $CH_2Cl_2$ (2 times for 2 min) (e) amino acid coupling: achieved by the method of D. Hudson, J. Org. Chem., 53, 617 (1988) using the appropriate protected amino acid (2 molar equivalents per mmol of the Boc-Leu-resin) and BOP (2 molar equivalents per mmol of the Boc-Leu-resin in the presence of DIPEA (6 molar equivalents providing pH8 for the reaction mixture) in $CH_2Cl_2$ or DMF; the reaction time for coupling varied from 3 to 5 h; and (f) wash: $CH_2Cl_2$ or DMF (2 times for 2 min each).

The Boc group gave $N^\alpha$ protection for the Leu, the first-added Asp and the Tyr residues. The Fmoc group gave $N^\alpha$ protection for the second-added (bridgehead) Asp, Ile and Val residues. Side chain protection was as follows: 2,6-dichlorobenzyl for the Tyr residue, Bzl for the first added Asp residue and $Bu^t$ for the bridgehead Asp residue.

After each coupling, the completeness of the reaction was checked by the ninhydrin test, E. Kaiser et al., Anal. Biochem., 34, 595 (1970).

On completion of the peptide sequence, the protected hexapeptide-resin was collected on a filter, washed with $CH_2Cl_2$ and EtOH and dried under reduced pressure for 24 h. The linear hexapeptide was cleaved from the hexapeptide-resin by photolysis of a suspension of the latter peptide-resin (350 mm, $-5°$ C., 6 to 24 h) in a mixture of DMF/EtOH (4:1). The resin was filtered and the filtrate was concentrated and the residue dried under reduced pressure.

The residual oil was dissolved in a mixture of DMF and $Et_2O$ at 0° C. and treated with diazomethane (0.3–0.5M in $Et_2O$). Excess diazomethane and solvents were removed under reduced pressure to give the protected linear intermediate of formula 2 wherein $A^1$ is absent, $R^3$ is 1-methylpropyl, $R^2$ is 1-methylethyl, $R^4$ is hydrogen, $R^{1A}$ is (4-(2,6-di ClBzl-O)phenyl)methyl, $R^5$ is 2-methylpropyl, $X^1$ is Boc, $X^2$ is $Bu^t$, $X^3$ is Bzl, Y is oxo and $Z^1$ is $OCH_3$.

The latter intermediate was dissolved in 50% TFA in $CH_2Cl_2$ at 0° C. and the solution was allowed to stand at that temperature for 1 h and then at 25° C. for 2 h. The completeness of the reaction was checked by reversed phase HPLC. On completion of the reaction, the solvents were removed from the reaction mixture under reduced pressure and the residual solid was triturated in $Et_2O$. The solid was collected on a filter and dried under reduced pressure to give the corresponding protected peptide of formula 3.

The preceding intermediate was dissolved in DMF containing 12 molar equivalents of diisopropylethylamine. The solution was added over 3 h to a solution of DMF containing 4 molar equivalents of BOP. The solvents were removed under reduced pressure and the residue was dissolved in a mixture of DMF and EtOH. The solution was stirred magnetically in the presence of 5% Pd/C under a hydrogen atmosphere for 12 h. The mixture was filtered through a 0.45 $\mu$m filter membrane and the filtrate was concentrated. The solid residue was dried under reduced pressure. The solid residue (i.e. the C-terminal methyl ester of the title compound) was dissolved in methanol and 1N aqueous lithium hydroxide (2:1). After standing at room temperature for 2 h, the hydrolysis mixture was poured into $H_2O$. The pH of the resultant mixture was adjusted to 7 by the addition of 1N aqueous HCl. The mixture was lyophilized.

Purification of the resulting solid residue to greater than 95% homogeneity was accomplished by reversed phase HPLC with a WATERS MODEL 590 programmable solvent delivery module (Milipore Corporation, Milford, Mass. USA) equipped with a UV detector and using a WHATMAN PARTISIL®10 ODS-3 C-18 column (octadecyl-silica) (2.2×50 $cm^2$), 10 micron particle size. The elution was done with a gradient of acetonitrile in 0.06% aqueous TFA as such:

a) initial: 10% acetonitrile in 0.06% aqueous TFA for 20 min, b) followed by gradually increasing the concentration of acetonitrile to 20% over a period of 20 min followed by gradually increasing the concentration to 40% acetonitrile over a period of 50 min.

Pure fractions, as determined by analytical HPLC, were pooled and lyophilized to afford the title cyclic peptide. Analytical HPLC showed the product to be at least 95% homogeneous. Amino acid analysis: Asp, 2.08; Val, 0.57; Ile, 0.57; Leu, 1.01; Tyr, 0.91; FAB-MS: calcd: 718.35, found: 719 $(M+H)^+$.

EXAMPLE 2

The cyclic peptide of formula 1a wherein $R^1$ is (4-hydroxyphenyl)methyl, $R^2$ is 1-methylethyl, $R^3$ is 1-methylpropyl, $R^4$ is methyl and $R^5$ is 2-methylpropyl was prepared by the procedure of example 1 except that Fmoc-N-Me-Val-OH was used instead of Fmoc-Val-OH. The cyclic peptide gave the following amino acid analysis and mass spectrum data: Amino acid analysis: Asp, 2.12; Ile, 0.95; Leu, 1.00: Tyr, 0.92, N-Me-Val, 1.28. FAB-MS: calcd: 732.84, found: 755 $(M+Na)^+$.

EXAMPLE 3

The cyclic peptide of formula 1b wherein $R^1$ is (4-hydroxyphenyl)methyl, $R^2$ is 1-methylethyl, $R^3$ is 1-methylpropyl, $R^4$ is hydrogen and $R^5$ is 2-methylpropyl was prepared by the procedure of example 1, coupling three additional Fmoc amino acids, i.e. Fmoc-Ala-OH, Fmoc-Gly-OH and Fmoc-Thr(Bzl)-OH, before coupling Boc-Tyr(2,6-diClBzl)-OH. The cyclic peptide gave the following amino acid analysis and mass spectrum date: Amino acid analysis: Asp, 2.41; Thr, 0.93; Gly, 1.02; Ala, 1.08; Val, 0.77; Ile, 0.10, Leu, 1.31; Tyr, 0.94. FAB-MS: calcd: 947, found: 948 $(M+H)^+$.

EXAMPLE 4

Inhibition of Herpes Simplex Virus (HSV, type 1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et al., J. Gen. Virol., 66, 733 (1985).

b) Assay and Results for Exemplified Peptides

The procedure described by P. Gaudreau et al., J. Biol, Chem., 262, 12413 (1987) was employed. Assay results for the exem-plified peptides of example 1, 2 and 3 are listed below. The assay result for each peptide is expressed as the concentration of the peptide producing 50% of the maximal inhibition ($IC_{50}$) of enzyme activity. The number of units of the enzyme preparation used in each assay was constant, based on the specific activity of the enzyme preparation. The results are relative to the activity obtained in control experiments without peptide and represent the mean of four assays that varied less than 10% with each other.

|  | $IC_{50}$ (μm) |
| --- | --- |
| Cyclic peptide of example 1 | 14.3 |
| Cyclic peptide of example 2 | 140 |
| Cyclic peptide of example 3 | 16 |

Other examples of the cyclic peptides of formula 1 are:

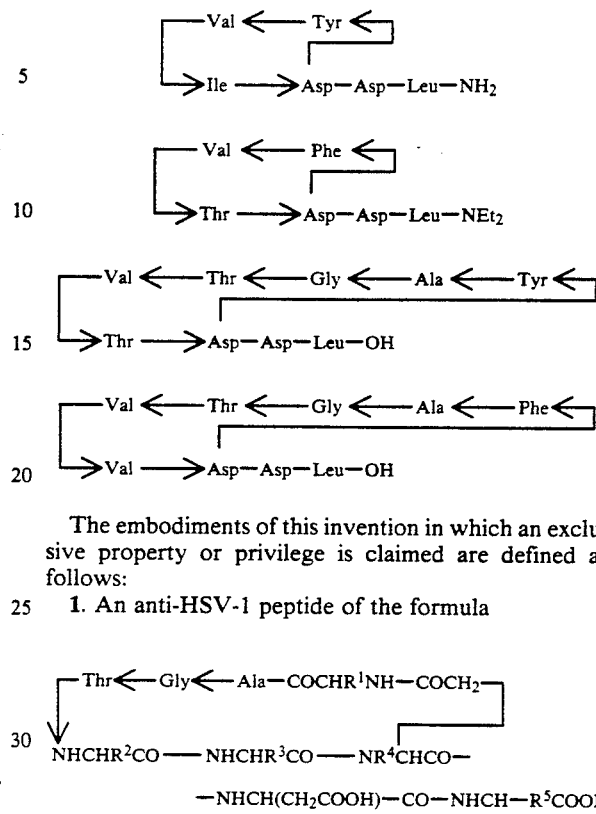

The embodiments of this invention in which an exclusive property or privilege is claimed are defined as follows:

1. An anti-HSV-1 peptide of the formula

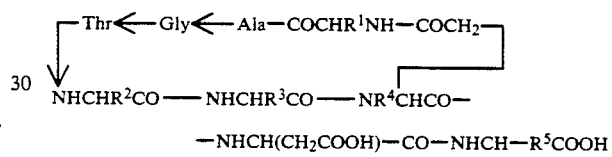

$$-NHCH(CH_2COOH)-CO-NHCH-R^5COOH$$

wherein
 $R^1$ is (4-hydroxyphenyl)methyl;
 $R^2$ is 1-methylethyl;
 $R^3$ is 1-methylpropyl;
 $R^4$ is hydrogen; and
 $R^5$ is 2-methylpropyl,
or a therapeutically acceptable salt thereof.

* * * * *